(12) United States Patent
Baer-Beck et al.

(10) Patent No.: US 11,238,627 B2
(45) Date of Patent: Feb. 1, 2022

(54) METHOD FOR THE RECONSTRUCTION OF AN IMAGE DATA SET OF COMPUTED TOMOGRAPHY, COMPUTED TOMOGRAPHY APPARATUS, COMPUTER PROGRAM AND ELECTRONICALLY READABLE DATA CARRIER

(71) Applicant: Siemens Healthcare GmbH, Erlangen (DE)

(72) Inventors: Matthias Baer-Beck, Erlangen (DE); Christian Hofmann, Erlangen (DE); Harald Schoendube, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 183 days.

(21) Appl. No.: 16/598,050

(22) Filed: Oct. 10, 2019

(65) Prior Publication Data

US 2020/0126272 A1  Apr. 23, 2020

(30) Foreign Application Priority Data

Oct. 19, 2018  (EP) .................................... 18201468

(51) Int. Cl.
*G06T 11/00* (2006.01)
*G06T 7/13* (2017.01)
(Continued)

(52) U.S. Cl.
CPC ............ *G06T 11/008* (2013.01); *A61B 6/032* (2013.01); *A61B 6/5247* (2013.01);
(Continued)

(58) Field of Classification Search
CPC .... H04N 13/204; A61B 6/5247; A61B 6/032; A61B 6/5258; A61B 6/54; G06T 11/008;
(Continued)

(56) References Cited

U.S. PATENT DOCUMENTS 8,155,415 B2 * 4/2012 Faul ..................... A61B 6/5235
382/131
9,495,769 B2  11/2016 Bruder et al.
(Continued)

FOREIGN PATENT DOCUMENTS

DE  102013220663 A1  4/2015

OTHER PUBLICATIONS

Ohnesorge, B. et al., "Efficient correction for CT image artifacts caused by objects extending outside the scan field of view", Med.Phys., vol. 27, No. 1, pp. 39-46, Jan. 2000.
(Continued)

*Primary Examiner* — Brenda C Bernardi
(74) *Attorney, Agent, or Firm* — Harness, Dickey & Pierce, P.L.C.

(57) ABSTRACT

A method is for the reconstruction of an image data set from projection images of an examination object recorded at different projection directions with a computed tomography apparatus. In an embodiment, the method includes establishing an item of contour information describing a contour of at least one of the examination object and the additional object; enhancing projection data of the projection images via forward projection in regions in which at least one of the examination object and the additional object was not acquired; and reconstructing the image data set based upon the projection data enhanced. The examination object and the additional object are acquired from sensor data of at least one camera. Finally, an item of sensor information at least partially describing at least one of the is of the examination object and of the additional object being established and used for establishing the contour information.

20 Claims, 3 Drawing Sheets

(51) Int. Cl.
*H04N 13/204* (2018.01)
*A61B 6/03* (2006.01)
*A61B 6/00* (2006.01)
*G06T 17/00* (2006.01)

(52) U.S. Cl.
CPC .............. *A61B 6/5258* (2013.01); *A61B 6/54* (2013.01); *G06T 7/13* (2017.01); *G06T 17/00* (2013.01); *H04N 13/204* (2018.05); *G06T 2207/10081* (2013.01)

(58) Field of Classification Search
CPC ......... G06T 7/13; G06T 17/00; G06T 11/005; G06T 2207/10081; G06T 2211/432
See application file for complete search history.

(56) References Cited

U.S. PATENT DOCUMENTS

2008/0319321 A1* 12/2008 Goldbach .............. A61B 5/444
 600/475
2011/0188723 A1 8/2011 Bruder et al.
2015/0103969 A1 4/2015 Flohr et al.
2018/0333081 A1* 11/2018 Hale ........................ G06T 7/74

OTHER PUBLICATIONS

Mahmoud Ismail et al.; "3D-Guided CT Reconstruction using Time-of-Flight Camera"; Proc. of SPIE; vol. 7964; Jan. 3, 2011; p. 796429-1-796429-11.

Cesare Jenkins et al; "Using a handheld stereo depth camera to overcome limited field-of-view in simulation imaging for radiation therapy treatment planning"; Medical Physics; vol. 44; No. 5; Apr. 17, 2017; pp. 1857-1864; XP055572464.

Kolditz et al; "Comparison of extended field-of-view reconstructions in C-arm flat-detector CT using patient size, shape or attenuation information";Physics in medicine and biology; vol. 56; 2011; p. 39-56; ISSN 1361-6560.

Hsieh J., et.al. : "A novel reconstruction algorithm to extend the CT scan field-of-view" Med. Phys. Nr. 31, vol. 9, pp. 2385-2391, Sep. 2004.

Extended European Search report for EP Application Patent No. 18201468, dated Apr. 1, 2019.

* cited by examiner

METHOD FOR THE RECONSTRUCTION OF AN IMAGE DATA SET OF COMPUTED TOMOGRAPHY, COMPUTED TOMOGRAPHY APPARATUS, COMPUTER PROGRAM AND ELECTRONICALLY READABLE DATA CARRIER

PRIORITY STATEMENT

The present application hereby claims priority under 35 U.S.C. § 119 to European patent application number EP 18201468.8 filed Oct. 19, 2018, the entire contents of which are hereby incorporated herein by reference.

FIELD

Embodiments of the invention generally relate to a method for the reconstruction of an image data set from projection images of an examination object recorded from different projection directions with a computed tomography apparatus, wherein the computed tomography apparatus has a nominal field of view which is acquired from all projection directions in the respective projection images, and wherein the examination object and/or an additional object associated with the examination object, in particular, with its positioning, extends partially out of the nominal field of view into an extended field of view, wherein for the reconstruction of the image data set an item of contour information describing the contour of the examination object and/or of the additional object is established, the projection data of the projection images is enhanced on the basis of the contour information by way of forward projection in regions in which the examination object and/or the additional object was not acquired in the projection data of a projection image, and the reconstruction takes place on the basis of the enhanced projection data. In addition, the invention relates to a computed tomography apparatus, a computer program and an electronically readable data carrier.

BACKGROUND

In computed tomography, lower-dimensional projection images, for example, one or two-dimensional projection images, of an examination object are recorded from different projection directions, for example, along a recording trajectory, in particular, a circular path. By way of known reconstruction methods, for example, filtered back projection, from the one-dimensional or two-dimensional projection images, two-dimensional slice images or three-dimensional volumes can be reconstructed as image data sets. For an artifact-free reconstruction, it is important that the examination object is acquired perpendicularly to the path of the recording trajectory in its full extent by way of all the projection images, wherein in typical computed tomography apparatuses, the space region that is acquired in all the projection directions is also designated the nominal field of view or "scan field of view" (sFoV). The nominal field of view therefore denotes the region within the computed tomography gantry that is entirely covered by the X-ray detector of the recording arrangement of the computed tomography apparatus.

However, investigation situations exist in which parts of the patient as the examination object are situated outside the nominal field of view and thus cannot be reconstructed with conventional reconstruction algorithms, or not artifact-free. This arises, for example, if the computed tomography imaging is used for the establishing of irradiation plans for radiotherapy. Thereby, special positioning aids are often used as additional objects, for example, head fixing device or chest holders. Through the use of the positioning aids, the possibilities for positioning the patient within the computed tomography apparatus, in particular the gantry, are significantly restricted, so that it cannot always be prevented that relevant parts of the patient are situated outside the nominal field of view. Apart from the use of special additional objects, in particular positioning aids, the constitution of the patient, for example in the case of obese patients, can also have the result that relevant regions of the patient are situated outside the nominal field of view. The nominal field of view can have a diameter, for example, of 500 mm.

In order also to be able to represent, directly and accurately in the image data set, portions of the patient not acquired in all the projection images and thus to ensure a correct diagnosis or a correct calculation of irradiation plans even in regions outside the nominal field of view, in the prior art, different methods have been proposed for a so-called reconstruction in the extended field of view (extended field of view reconstruction) have been proposed. A class of procedures that are known thereby provides that firstly an initial estimation of the contour of the examination object, usually the patient, is also established in regions outside the nominal field of view as contour information. This contour information is then used in a further step to enhance projection data of the projection images outside the nominal field of view, in order then to enable the most accurate possible reconstruction of the image data set, even in an extended field of view that is larger than the nominal field of view.

It is thereby known, for example, firstly to undertake an initial reconstruction of a preliminary data set from the projection data, whereby extrapolation methods can be used which prevent an occurrence of so-called truncation artifacts, so that the scanned computed tomography data can be extrapolated into regions outside the X-ray detector that were not acquired during the scan. In this regard, reference is made to the article by J. Hsieh et al., "A novel reconstruction algorithm to extend the CT scan field-of-view", Med. Phys. 31(9), pages 2385-2391 (2004), and the article by B. Ohnesorge et al., "Efficient correction for CT image artifacts caused by objects extending outside the scan field of view", Med. Phys. 27(1), pages 39-46 (2000).

Following an initial reconstruction of a preliminary data set, the contour of the examination object, specifically the patient, can take place, for example, on the basis of threshold value methods, so that therefore the contour information can be a binary image of the patient, which classifies the initially reconstructed image data set, typically, into regions which contain air and those which contain the examination object and/or, where relevant, additional objects, for example, positioning aids. Such contour information, in particular binary images, can be used to enhance by forward projection and lacking projection data in the projection images as faithfully as possible to the original, for example, in that in the context of the forward projection, HU values that are typical for patients, for example those of water, are assigned to these patient voxels. With projection data or projection images enhanced on the basis of such a forward projection, an image data set that is as correct as possible is obtainable also in regions outside the nominal field of view. For the establishment of an item of contour information from a reconstruction data set obtained in an initial reconstruction, reference is made, in particular, to US 2011/0 188 723 A1 and U.S. Pat. No. 9,495,769 B2.

Nevertheless, such initial reconstructions that take place on the basis of the originally recorded projection images are not obtained entirely artifact-free or can contain errors, in particular, in regions which are obtained in only very few projection images (or not at all) in the original projection data.

SUMMARY

At least one embodiment of the invention is directed to improving the reconstruction quality in reconstructions of computed tomography image data sets in extended fields of view that are larger than the nominal field of view.

Embodiments are directed to a method, a computed tomography apparatus, a computer program and an electronically readable data carrier. Advantageous developments are disclosed in the claims.

In at least one embodiment of the invention, a method includes, from sensor data of at least one camera, acquiring the examination object positioned for the recording of the projection images and/or the additional object, an item of sensor information at least partially describing the contour of the examination object and/or of the additional object is established and is used for establishing the contour information.

According to at least one embodiment of the invention, it is therefore proposed to establish the contour of the examination object or, if an additional object protrudes out of the nominal field of view, of the additional object not or at least not exclusively on the basis of an initial reconstruction from the originally recorded projection images, but to utilize an additional sensor system, in the present case, in particular, optical cameras arranged in the proximity of the computed tomography apparatus or the examination object positioning site, in order thereby to obtain more accurate and more reliable information regarding the corresponding contours in the form of the sensor information and to use it for the establishment of the contour information. In the actual case, this means that an embodiment of the present invention relates to the establishment of the contour information that is needed in the method that is known in principle from the prior art, for reconstruction in the extended field of view. In concrete terms, it is proposed in one example to determine the patient contour using one or more additional cameras which can be arranged, for example, on the ceiling above the patient table. With the aid of cameras, it is possible to acquire the real surface of the examination object and its position in space during the examination procedure with the computed tomography apparatus. This additional sensor data from which, as sensor information, the position and form of the contour can be established is then used in the form of the sensor information in order to establish the contour information which is then used to enhance projection images as correctly as possible and to obtain high quality information that is as artifact-free as possible in the context of the reconstruction of the image data set. The measurement with cameras enables the scanned projection data to be enhanced as correctly as possible in regions which have not been acquired by the X-ray detector, that is, with the greatest possible agreement with the reality.

Alongside the method, at least one embodiment of the present invention also relates to a computed tomography apparatus comprising at least one camera and a control device configured for carrying out the method according to at least one embodiment of the invention. All the embodiments relating to the method according to embodiments of the invention can be transferred similarly to the inventive computed tomography apparatus with which the advantages mentioned above can therefore also be obtained. In particular, the computed tomography apparatus can comprise a recording arrangement, comprising an X-ray tube assembly and an X-ray detector, wherein the recording arrangement can be, for example, movably mounted in a gantry. For the positioning of the examination object, the computed tomography apparatus can further comprise a patient table. The control device can comprise at least one processor and at least one storage device. In concrete terms, for carrying out at least one embodiment of the inventive method, the control device can comprise, for example, a reconstruction unit for reconstructing image data sets and/or reconstruction data sets for preliminary information, a sensor information establishing unit, a contour information establishing unit, a forward projection unit and an enhancing unit.

A computer program according to at least one embodiment of the invention is, for example, directly loadable into a memory store of a control device of a computed tomography apparatus and has program code in order to carry out the steps of at least one embodiment of an inventive method when the computer program is executed in the control device of the computed tomography apparatus. The computer program can be stored on an inventive electronically readable data carrier which therefore comprises electronically readable control information stored thereon, which comprises at least one inventive computer program and is configured such that, on use of the data carrier in a control device of a computed tomography apparatus, said control information carries out an inventive method. The data carrier can be, in particular, a non-transient data carrier, for example, a CD-ROM.

At least one embodiment of the present application is directed to a computed tomography apparatus, comprising:

at least one camera; and a control device configured for reconstructing an image data set from projection images of an examination object recorded at different projection directions with a computed tomography apparatus, the computed tomography apparatus including a nominal field of view acquired from all projection directions in the respective projection images, at least one of the examination object and an additional object associated with the examination object extending partially out of the nominal field of view into an extended field of view, the control device being configured to:

establish an item of contour information describing a contour of at least one of the examination object and the additional object;

enhance projection data of the projection images, based upon the contour information established, by way of forward projection in regions in which at least one of the examination object and the additional object was not acquired in the projection data of a projection image; and reconstruct the image data set based upon the projection data enhanced, wherein, from sensor data of at least one camera, the examination object positioned for recording at least one of the projection images and the additional object is acquired, an item of sensor information at least partially describing at least one of the contour of the examination object and of the additional object being established and used for establishing the contour information.

At least one embodiment of the present application is directed to a non-transitory computer readable medium storing program code to carry out the method of at least one embodiment when the program code is executed on a control device of a computed tomography apparatus.

At least one embodiment of the present application is directed to an electronically readable data carrier storing a computer program to carry out the method of at least one embodiment when the program code is executed on a control device of a computed tomography apparatus.

BRIEF DESCRIPTION OF THE DRAWINGS

Further advantages and details of the present invention are disclosed in the example embodiments described below and by reference to the drawings, in which.

DETAILED DESCRIPTION OF THE EXAMPLE EMBODIMENTS

Figure 1:
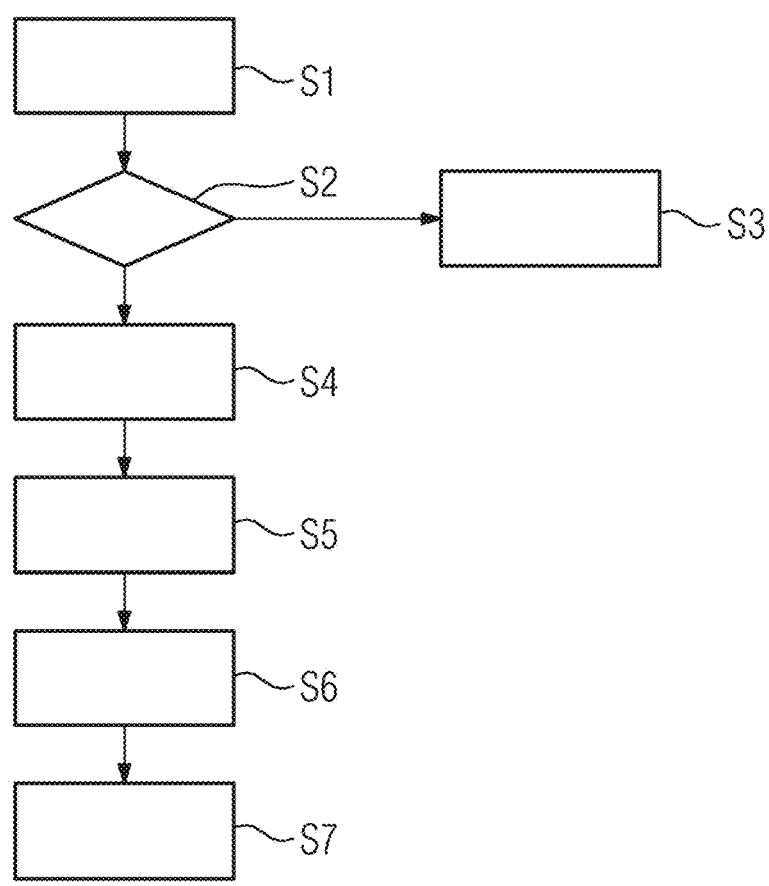
FIG. 1 shows a flow diagram of an example embodiment of the method according to the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In at least one embodiment of the invention, a method includes, from sensor data of at least one camera, acquiring the examination object positioned for the recording of the projection images and/or the additional object, an item of sensor information at least partially describing the contour of the examination object and/or of the additional object is established and is used for establishing the contour information.

Since computed tomography is used mainly in the field of medicine, the examination object is, in particular, a patient. Therefore, a plurality of examples relate in the following to a patient as the examination object, wherein, however the present invention is also applicable to other examination objects, for example in materials testing.

According to at least one embodiment of the invention, it is therefore proposed to establish the contour of the examination object or, if an additional object protrudes out of the nominal field of view, of the additional object not or at least not exclusively on the basis of an initial reconstruction from the originally recorded projection images, but to utilize an additional sensor system, in the present case, in particular, optical cameras arranged in the proximity of the computed tomography apparatus or the examination object positioning site, in order thereby to obtain more accurate and more reliable information regarding the corresponding contours in the form of the sensor information and to use it for the establishment of the contour information. In the actual case, this means that at least one embodiment of the present invention relates to the establishment of the contour information that is needed in the method that is known in principle from the prior art, for reconstruction in the extended field of view. In concrete terms, it is proposed in one example to determine the patient contour using one or more additional cameras which can be arranged, for example, on the ceiling above the patient table. With the aid of cameras, it is possible to acquire the real surface of the examination object and its position in space during the examination procedure with the computed tomography apparatus. This additional sensor data from which, as sensor information, the position and form of the contour can be established is then used in the form of the sensor information in order to establish the contour information which is then used to enhance projection images as correctly as possible and to obtain high quality information that is as artifact-free as possible in the context of the reconstruction of the image data set. The measurement with cameras enables the scanned projection data to be enhanced as correctly as possible in regions which have not been acquired by the X-ray detector, that is, with the greatest possible agreement with the reality.

An improved image quality of reconstructions in an extended field of view (eFoV), extended relative to the nominal field of view can contribute thereto that computed tomography apparatuses of which the nominal field of view is restricted as compared with other computed tomography apparatuses also become competitive since reconstructions can be performed in excellent image quality even beyond the nominal field of view.

Suitably, a camera configured as a 3D camera, in particular, an optical or terahertz camera can be used and/or at least one item of 3D information relating to the contour of the examination object and/or of the additional object can be established from sensor data of at least two differently positioned cameras and/or from an item of arrangement information of the camera. Preferably, in the context of the present invention, 3D cameras are used, for example, therefore optical 3D cameras and/or terahertz cameras. These directly provide three-dimensional sensor data relating to the objects acquired by them, in particular therefore, the examination object and/or the additional object. It is, however, also conceivable to establish, for example, three-dimensional information on the basis of two-dimensional cameras acquiring the examination object and/or the additional object from different directions, for example, stereoscopic cameras, or even, given knowledge of the arrangement and the acquisition geometry, to draw conclusions about relevant three-dimensional information from the data of a single two-dimensional camera. As mentioned above, it is however preferred in the context of the invention to use 3D cameras, in particular optical 3D cameras. The use of optical cameras has the further advantage that the sensor data can also be evaluated with regard to optical information, for example, for the identification of specific additional objects, as will be discussed in greater detail below.

In a suitable further development, it can also be provided that portions of the contour lying outside the acquisition range of a camera can be acquired by at least one further camera. For example, due to the position or the anatomy of a patient as the examination object, it can occur that parts of the patient or of the surface of the patient cannot be acquired by a single camera. A similar principle can apply to additional objects. In order, nevertheless to ensure a sufficient quantity of information, a plurality of cameras arranged at different sites in the space and having corresponding acquisition ranges can be used.

Suitably, it can be provided that the camera is and/or will be registered with a recording arrangement of the computed tomography apparatus and/or in the case of a plurality of cameras, these are or will be registered among one another. On a registration, location information contained in the sensor information can also be used directly in the coordinate system in which the computed tomography recording takes place. At least during a registration or the like, protruding starting positions arise. Thereby, a permanently present registration is conceivable, based upon a fixed arrangement of the camera relative to other components of the computed tomography apparatus. On the other hand, however, it is naturally also possible to undertake a registration explicitly, for example, by using phantoms and/or markers visible both in the sensor data of the camera and also in X-ray images of the computed tomography apparatus. It should be noted at this point that a registration must not necessarily exist between the camera and the recording arrangement of the computed tomography apparatus since, for example, surfaces of examination objects can be registered by way of the contours for performing registrations on the basis, also, of a roughly known positional relationship easily obtained in the context of an initial reconstruction of preliminary information obtained from the original projection data.

Preferably, a portion of the contour of the examination object, in particular a covered portion of the contour, not acquirable by the at least one camera can be established by extrapolation and/or interpolation, in particular using a patient model. This means, for example for portions of the surface of a patient that are covered by the patient table and/or additional objects and/or other portions of the patient, that lacking information can be established, for example, by suitable interpolation or extrapolation methods. It is particularly preferred, however, to use, in particular, a statistical patient model which describes the outer contour of an average patient which can then be adapted to the known portions of the contour of the examination object on the actual patient, so that conclusions can be drawn regarding the lacking portions of the contour. It should be noted that such unknown portions can also be excluded from further use and can thus be marked, for example, as unknown.

In a concrete embodiment of the present invention, it can be provided that as an item of contour information, a binary subdivision, at least classifying according to air and examination object and/or additional object, at least of the extended field of view is used. This means that the contour information can be present as a type of "binary image" or, in general, a "material class image" since such like is outstandingly suitable as a starting point for a forward projection if therein, the regions marked as "object" are filled as corresponding HU values or if what is concerned is only the determination of the limitation of the examination object and/or of the additional object within the projection images that are to be enhanced of particular projection directions. Finally, such a binary image can be understood as subdivided into two material classes. It should be noted that embodiments are also conceivable and advantageous in which more than two material classes are used. In particular, for example, a distinction can also be made between additional objects and examination objects, which is suitable, in particular, if the additional object has an attenuation property that is clearly different from the patient, but which is known. Different material types can possibly also be represented in the additional object over a plurality of material classes.

In principle, it is advantageously conceivable within the context of at least one embodiment of the present invention that the establishment of the contour information takes place proceeding from the sensor information or even, if the portions of the examination object and/or of the additional object protruding beyond the nominal field of view are described completely and, in particular, sufficiently accurately by way of the sensor data, as the sensor information. Since it can be assumed that the sensor data reproduces the examination object and/or the additional object sufficiently exactly and reliably, in particular, on complete reproduction of the at least one object, therefore, a binary image or an image classified into more than two material classes can be established and taken as the basis for the forward projection. It is also conceivable, however, for example, to undertake an enhancement of the sensory information from preliminary information established from a provisional reconstruction from the original projection images for the establishment of the contour information.

It is however also conceivable in another embodiment of the present invention if, firstly through reconstruction of a provisional reconstruction data set from the original projection images for the extended field of view and threshold value formation, an item of preliminary information provisionally describing at least the contour of the examination object and/or of the additional object is established, said preliminary information being adapted on the basis of the sensor information. In the example of a patient, a binary image or, generally, an image classified into a plurality of material classes (material class image), in particular, a classification of voxels into air and patient, also from an initial reconstruction of the scanned original projection images, in particular, by way of threshold value formation, can be created. This initial reconstruction can be carried out, for example, as in the prior art mentioned in the introduction, especially for extended fields of view, in order for example to reduce or prevent truncation artifacts. However, a simple initial reconstruction can also take place based only on the scanned projection data.

The sensor information obtained from the sensor data of the at least one camera regarding the position and shape of the surface of the examination object, in the example of the patient, can now be used to improve the contour of the examination object established from the threshold value formation, above all in regions above the nominal field of view of the computed tomography apparatus. For this purpose, it can be provided, in particular, that the adaptation of the preliminary information to the contour information takes place through elastic registration of the preliminary information to components of the contour contained in the sensor information. Therefore, for example, the contour created from the initial reconstruction of the original projection data can be adapted by way of a suitable registration algorithm so that after the registration, the contour of the examination object coincides with the position of the examination object surface, in particular, the patient surface determined from the sensor data of the at least one camera. A similar process can naturally also be carried out in relation to additional objects, the surface of which can also be estimated from the sensor data of the at least one camera and used as sensor information. If parts of a surface or contour cannot be acquired by the at least one camera and no suitable interpolation appears possible, these parts can also be excluded from the registration, wherein, however, an elastic registration can nevertheless provide at least for a smooth transition.

With regard to additional objects, it should be noted at this point that artifacts in image data sets can also occur even if, although the examination object is fully contained within the nominal field of view, an additional object, for example, for positioning an examination object, such as a head fixing device for a patient, protrudes out of the nominal field of view. In this regard, the contour determination must not necessarily relate (exclusively) to the examination object, in particular, the patient, but can also relate to additional objects, for example, head fixing device, chest holders and such like.

Apart from the direct use of sensor data of the at least one camera with regard to the examination object surface, the sensor data of the at least one camera can thus be used to recognize particular additional objects that are situated in the extended field of view. This is suitable, in particular, as set out below, with additional objects for which exact three-dimensional computer models, for example CAD models and/or design drawings exist. This is often the case, for example, for positioning aids and/or patient tables as additional objects. Then, such a three-dimensional computer model of the additional object can also suitably be used in order to improve the calculation of the contour information.

A development of at least one embodiment of the present invention accordingly provides that, from the sensor data, at least one item of object information describing the type of the additional object used, in particular, for supporting and/or for positioning the examination object for which additional object a three-dimensional computer model, in particular a CAD model exists, is established, wherein the three-dimensional computer model is used in the establishment of the contour information describing the contour of the additional object. Thereby, it can be specifically provided that, on the basis of the object information, the three-dimensional computer model of the additional object is selected, after which the contour of the additional object is adapted, according to the sensor information and/or the preliminary information for the establishment of the contour of the additional object in the contour information, to the three-dimensional computer model of the additional object, in particular, in its position and/or through rigid or elastic registration. In particular, herein, it can be specified on the basis of the sensor information and/or the preliminary information, that is, the best matching position of the three-dimensional computer model that is assumed to be rigid, whereupon the surface described by the three-dimensional computer model in this position is used in the contour information as the contour of the additional object. It should be noted at this point that the object information can be established particularly easily if, by way of the at least one camera, optical sensor data is recorded, since it provides important information for the identification of an additional object.

If, therefore, an additional object is recognized with the aid of the at least one camera, its three-dimensional computer model, for example, a CAD model can be made use of accordingly to improve the contour information, in particular, in that the three-dimensional computer model is adapted to an initial reconstruction of the original projection images, as described above as preliminary information, with regard to its position in the space. From the three-dimensional computer model adapted, with regard to its position, to the initial reconstruction, a binary image or an image with a plurality of material classes can, in turn, be created which, if necessary, can also contain a contour of the examination object, but then preferably also assigns voxels to the additional object and/or to the examination object.

It should be noted at this point that a use of the three-dimensional computer model of the additional object is also suitable for a direct establishment of the contour information from the sensor information, since the three-dimensional computer model can be understood as reproducing the reality and can thus also, for example, compensate for scan errors or such like in the sensor data of the at least one camera, in that it is fitted into the contour of the additional object determined in the sensor information and replaces said information. Thereby, it is particularly suitable that due to the three-dimensional model, both on its use in the sensor information and also on its use in the preliminary information, limitations of the additional object not visible to the camera also become known, which is suitable, in particular, if assigned HU values are to be used in the forward projection, wherein different HU values are to be assigned to the additional object and the examination object.

In this context, it is also particularly advantageous if the three-dimensional computer model of the additional object also comprises an item of material information describing attenuation properties for X-ray radiation in the additional object, said material information being taken into account in the forward projection. If, therefore, apart from the geometric model of the additional object, information regarding its material composition is available, this can be used further to improve the contour image of the additional object for the forward projection, in that regions within the additional object can be set to the correct HU value. In particular, for the irradiation planning, the correctness of the HU values (or, in general, attenuation values) are of great significance, since the correctness of the irradiation planning, in particular, as regards the dose distribution stands in direct relation to the correctness of the HU (Hounsfield Unit) values.

As previously stated, based upon the contour information established with the aid of the sensor data of the at least one camera, virtual projection data can be created by way of forward projection which can be used in a further step to enhance the scanned original projection data in regions outside the nominal field of view.

In a particularly preferred development of at least one embodiment of the present invention, it can be provided that for each scan with the computed tomography apparatus, the sensor information is automatically checked for portions of the examination object and/or the additional object protruding outside the nominal field of view, whereby the reconstruction is automatically triggered with or without an extended field of view. This means that the evaluation of the sensor data of the at least one camera can take place for every investigation with the computed tomography apparatus in order to classify these investigations into those which need an extended field of view and those for which the nominal field of view is sufficient. This means that the sensor information regarding the position and shape of the examination object or additional objects can be used to switch an algorithm for reconstruction in an extended field of view on or off automatically. Currently, this step is typically carried out manually by an operator of the computed tomography apparatus. Therefore, the decision on the necessity of the use of a special algorithm for the reconstruction in the extended field of view is made automatically on the basis of the sensor data of the at least one camera.

Alongside the method, at least one embodiment of the present invention also relates to a computed tomography apparatus comprising at least one camera and a control device configured for carrying out the method according to at least one embodiment of the invention. All the embodiments relating to the method according to embodiments of the invention can be transferred similarly to the inventive computed tomography apparatus with which the advantages mentioned above can therefore also be obtained. In particular, the computed tomography apparatus can comprise a recording arrangement, comprising an X-ray tube assembly and an X-ray detector, wherein the recording arrangement can be, for example, movably mounted in a gantry. For the positioning of the examination object, the computed tomography apparatus can further comprise a patient table. The control device can comprise at least one processor and at least one storage device. In concrete terms, for carrying out at least one embodiment of the inventive method, the control device can comprise, for example, a reconstruction unit for reconstructing image data sets and/or reconstruction data sets for preliminary information, a sensor information establishing unit, a contour information establishing unit, a forward projection unit and an enhancing unit.

A computer program according to at least one embodiment of the invention is, for example, directly loadable into a memory store of a control device of a computed tomography apparatus and has program code in order to carry out the steps of at least one embodiment of an inventive method when the computer program is executed in the control device of the computed tomography apparatus. The computer program can be stored on an inventive electronically readable data carrier which therefore comprises electronically readable control information stored thereon, which comprises at least one inventive computer program and is configured such that, on use of the data carrier in a control device of a computed tomography apparatus, said control information carries out an inventive method. The data carrier can be, in particular, a non-transient data carrier, for example, a CD-ROM.

FIG. 1 shows a flow diagram of an example embodiment of the method according to the invention. This is carried out on a computed tomography apparatus which, for example, has a recording arrangement with an X-ray detector and an X-ray tube assembly moved in a gantry. A patient as the examination object can be placed on a patient positioning device, in particular a patient table. Hereby, as additional objects, positioning aids, for example, head fixings and/or chest holders can be used. The computed tomography apparatus has a, for example cylindrical, nominal field of view in which projection data from all the projection directions of the recording arrangement can be recorded.

Further associated with the computed tomography apparatus are one or more optical 3D cameras which can record sensor data of a patient arranged on the patient positioning device, in particular, in the region of the nominal field of view.

In a step S1 carried out in each examination of a patient, an item of sensor information is determined which describes the shape of surfaces, that is contours, of the patient and possibly an additional object at least partially situated in the nominal field of view, for example, a positioning aid. For this purpose, the available three-dimensional sensor data is evaluated accordingly.

Thereby, different representations of the sensor information are conceivable, for example, a description of the surfaces which form the contours per se, although it is preferable to use a binary image or even an image divided into more than two material classes as sensor information. A binary image is differentiated between "air" and "material" (that is, examination object or additional object); an image using more material classes has the advantage that, for example, a distinction can also be drawn between additional objects and the examination object or even within these objects, in particular at least one additional object, regarding which, an item of material information comprises a corresponding item of structural information. Such a binary image or an image classifying voxels into a plurality of material classes can otherwise also be obtained in step S1 without the surfaces of the patient and possibly of the at least one additional object being entirely acquired, after which a completion of the surface of the patient can be undertaken on the basis of a particular, especially static, patient model, which is adapted to the surface portions acquired by at least one 3D camera. For additional objects, it is the case that by reason of the sensor data from the at least one 3D camera, certainly involving optical sensor data, they can be identified since an item of object information is established which describes the type of the additional object. Different three-dimensional computer models are thereby assigned to different items of object information, in the present case, CAD models (computer-aided/assisted-design models). Such three-dimensional computer models of additional objects can be inserted exactly fitting on the basis of the known portions of the surface of the additional object from the sensor data into such an image of the sensor information subdivided according to material classes.

In a step S2, on the basis of the sensor information, it is then checked whether parts of the patient and/or at least of one additional object protrude in an interfering manner out of the nominal field of view into the reconstruction of a computed tomography image data set planned on the basis of projection images, in particular therefore in a plane in which the recording arrangement or at least the X-ray tube assembly describes a circular path in the gantry as the recording trajectory (thus, with a cylindrical nominal field of view, out of the cylindrical envelope). This will now be described in greater detail by reference to FIG. 2.

Figure 2:
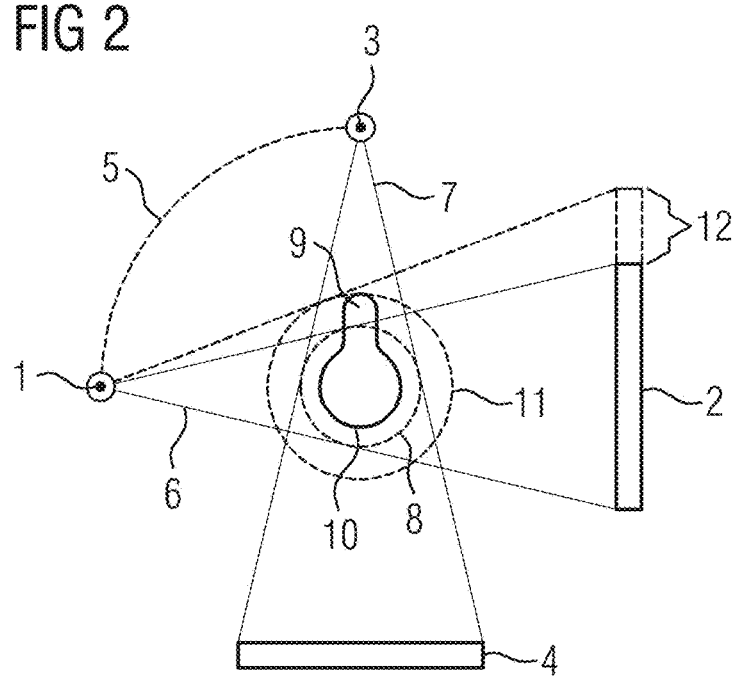
FIG. 2 shows a sketch illustrating the truncation of an examination object.

FIG. 2 shows with the aid of pairs of positions 1, 2 and 3, 4 of the X-ray tube assembly (positions 1, 3) and of the X-ray detector (positions 2, 4) the image recording in different projection directions along a circular recording trajectory 5, indicated by the respective radiation fields 6, 7. Evidently, the extents of the radiation fields 6, 7 and the further possible radiation fields define the nominal range of view 8 of the computed tomography apparatus, which means that object portions situated within the nominal range of view 8 are fully acquired by the X-ray detector and can therefore be correctly reconstructed, for example, in the context of a filtered back projection. In the present case, however, a portion 9 of the indicated examination object 10 protrudes out of the nominal field of view 8, so that it is acquired in the radiation field 7 by the X-ray detector, but not in the radiation field 6. If, in order to acquire the entire examination object 10, a reconstruction is simply carried out in the extended field of view 11 including the portion 9, artifacts could arise, in particular so-called truncation artifacts, for which reason special algorithms are used.

In the class of algorithms used in the case of a protrusion out of the nominal field of view 8 for the reconstruction in the extended field of view 11, projection images which show the examination object 10 truncated, for example, according to the radiation field 6 are enhanced with virtual projection data, in the present case in the region 12 indicated dashed. Thereby, as set out in further detail below, a forward projection is carried out, which in the case shown in FIG. 2 demands the most precise possible knowledge regarding the contour of the examination object 10, and with a protruding additional object, additionally or alternatively, exact knowledge of the contour of the additional object.

Step S2 (see FIG. 1 again) now serves for deciding whether such algorithms are needed for reconstruction in an extended field of view 11. This takes place fully automatically on the basis of the sensor information established in step S1, which means that checking is performed automatically of whether all the portions of the examination object 10 and, if relevant, the at least one additional object (which is not X-ray transparent) are situated within the nominal field of view 8. If this is the case, in step S3 the process continues with a normal, typical recording and reconstruction of an image data set which here is three-dimensional, whereby the reconstruction remains restricted to the nominal field of view 8.

If, however, it is ascertained that an object protrudes in a relevant manner out of the nominal field of view (in a plane in which the recording trajectory 5 extends), the process continues with a step S4 in which an item of contour information is established which is to be taken as the basis for a forward projection to be carried out in step S5 for establishing the projection data that is to be enhanced. For this purpose, different embodiments exist which are to be discussed below and can all be realized with the method of FIG. 1.

It is thus firstly conceivable to use the sensor information directly as contour information, since it has been obtained in an extremely reliable manner with exactly measuring optical 3D cameras. This is always useful if, for example, through the use of a patient model and/or three-dimensional computer models, even the unacquired portions of the surface of the respective relevant objects can be estimated highly accurately.

It is also possible, however, in an alternative embodiment in step S4 to proceed from an item of preliminary information which also describes the at least one relevant contour, which is determined by the initial reconstruction of the originally recorded projection images. This means that before the performance of step S4, in a step not shown in FIG. 1, the available two-dimensional projection images of the patient had been recorded along the recording trajectory 5 so that now they are present showing the examination object 10 and/or if relevant an additional object, partially truncated. Nevertheless, from these projection images, a reconstruction can be carried out also in the extended field of view 11 which possibly contains errors, wherein compared with the prior art set out in the introduction, methods have been proposed for at least reducing the number of errors. This initial reconstruction defines the relevant object, in the case of FIG. 2, the examination object 10 and thus its contour, including in the extended field of view 11. For example, in a threshold value-based method (threshold value comparison), for example, a binary image, therefore a material class image subdivided into "air" and "examination object 10" can be established as preliminary information from the reconstruction data set established in the initial reconstruction. The patient contour described thereby is then adapted by way of an elastic registration algorithm so that, after the registration, it matches the position of the patient surface present in the sensor information. This is a suitable procedure, in particular, if the contour of the examination object 10 was able only partially to be determined highly accurately by way of the sensor information.

It should be noted at this point that for simplification of the procedures described here, a registration between the at least one optical 3D camera and the coordinate system in which the projection images are acquired with the recording arrangement can already exist. Such a registration can be carried out, for example, by way of a phantom visible in both modalities.

In the case of an additional object protruding out of the nominal field of view 8 and/or to be taken into account in another way, otherwise in step S4 also, the previously mentioned three-dimensional computer model can be utilized. For example, by way of the sensor information containing an item of object information, the additional object can be identified and the correct three-dimensional computer model can be selected. This three-dimensional computer model, in particular CAD model, can now be adapted to the initial reconstruction of the projection data (and/or also the sensor information) with regard to its position in space. From the three-dimensional model adapted with regard to its position to the contour shapes in the reconstruction data set an, at least with regard to the additional object, binary image (not-object and object) can, in turn, be created, wherein advantageously, a combination with a corresponding binary image of the examination object 10 can take place in order to obtain a material class image subdivided into three or more material classes. It should be noted that the three-dimensional computer model of the additional object can also comprise an item of material information which defines attenuation properties, and which can possibly further subdivide the additional object into material classes, which is suitable with regard to the forward projection in step S5.

Figure 3:
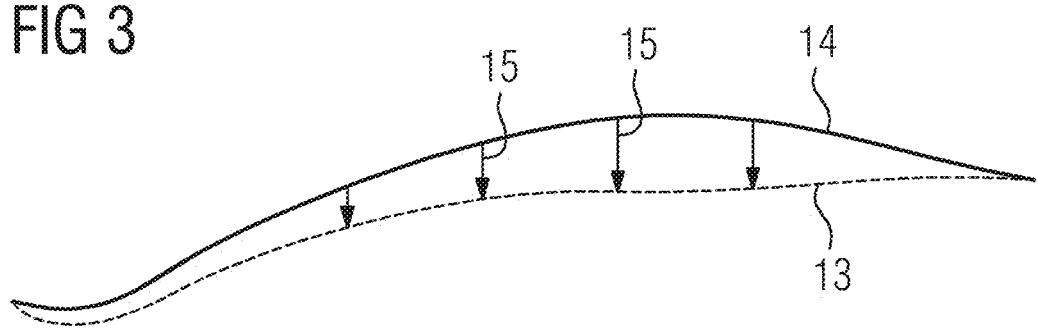
FIG. 3 shows the elastic registration of the contour of an item of preliminary information to a contour of an item of sensor information.

FIG. 3 shows, in more detail, aspects of these different approaches using an item of preliminary information. It is illustrated in FIG. 3 that a contour 13 (dashed) contained in the sensor information can deviate from a contour 14 (continuous) contained in the preliminary information and by way of elastic registration (see arrows 15), can be adapted accordingly in order to generate the contour information.

Figure 4:
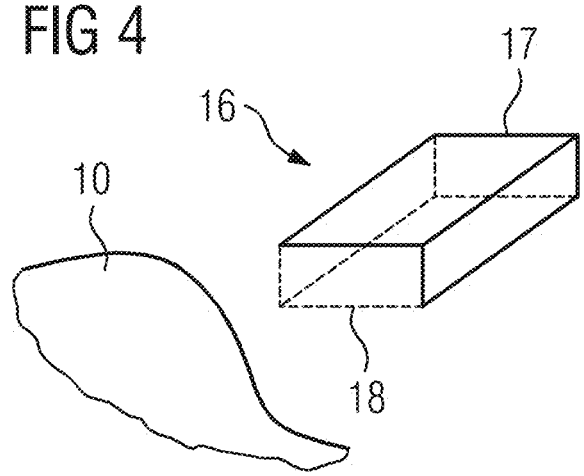
FIG. 4 shows a schematic explanation of the use of a three-dimensional computer model of an additional object.

FIG. 4 shows the enhancement of a contour of an additional object 16 shown here cuboid-shaped for simplification, by way of a three-dimensional computer model. For example, portions 17 (continuous) of the contour of the additional object 16 can already be known. By adaptation of the three-dimensional computer model, portions 18 shown dashed that are not yet or not yet exactly known can also be enhanced.

In a step S5 (see FIG. 1 again), the contour information established in step S4 is used to establish projection data to be used for enhancement in step S6 in the context of a forward projection. Thereby, in particular, in the advantageous embodiment in which a material class image has been created as contour information, HU values can be assigned to the corresponding material classes, for example, to the examination object 10, that is, to the patient, the HU value of water and an additional object 16, HU values which result from an item of material information assigned to the three-dimensional computer model. The enhancement resulting from the forward projection in step S5 is represented by step S6. Herein, for example, smooth transitions to the actually scanned projection data of the original projection images can be created.

Then, in step S7, the reconstruction of the computed tomography image data set which here is three-dimensional by reason of the two-dimensional projection images takes place from the enhanced projection images in the extended field of view 11, so that by reason of the exact establishment of the contour, high-quality image data is obtained.

Figure 5:
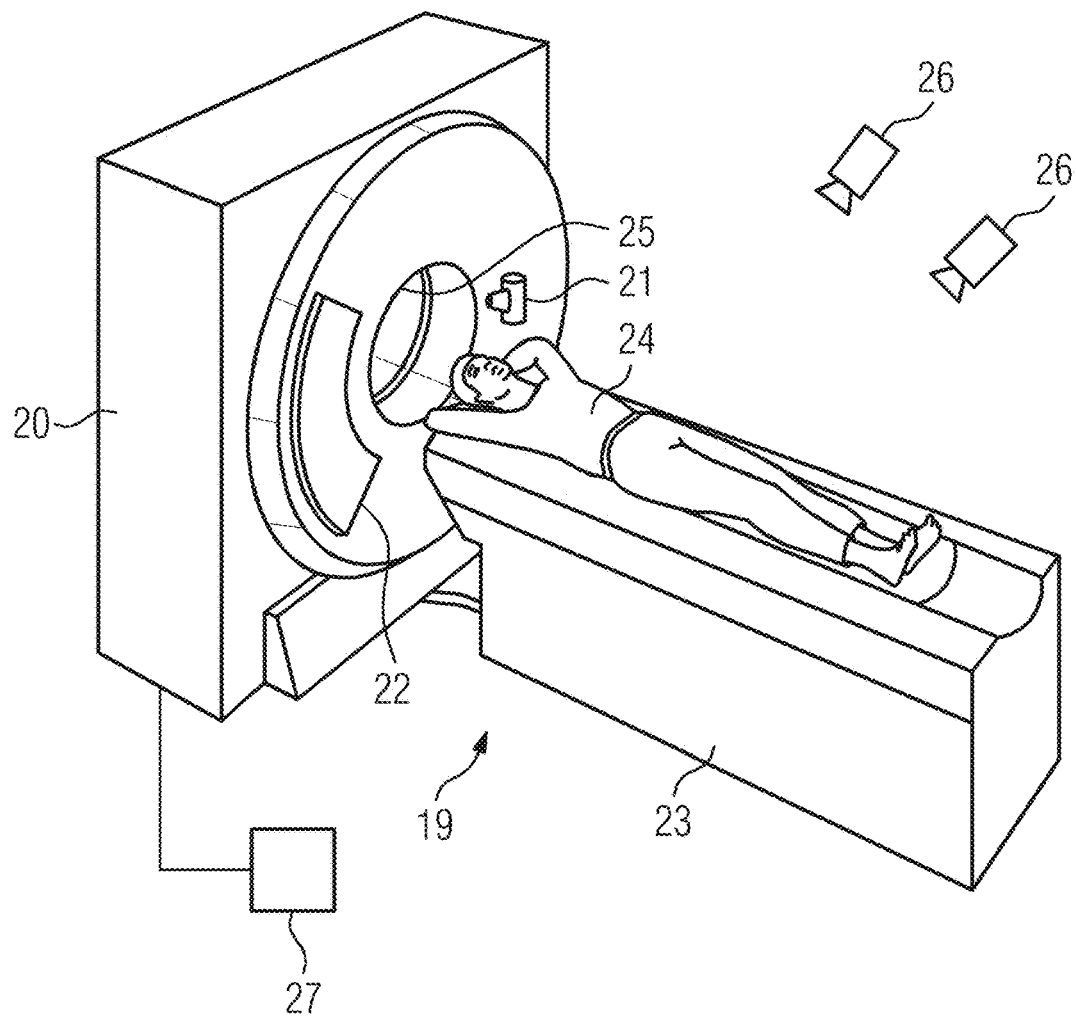
FIG. 5 shows an embodiment of an inventive computed tomography apparatus.

FIG. 5 shows a sketch of the principle of a computed tomography apparatus 19 according to the invention. This comprises, as is known in principle, a gantry 20 in which the recording arrangement comprising an X-ray tube assembly 21 and an X-ray detector 22 is rotatably mounted. The patient 24 positioned on a patient table 23 can be moved into a patient receiving space 25 of the gantry 20.

In the present case, the computed tomography apparatus 19 comprises, by way of example, two ceiling-mounted cameras 26 which are configured as optical 3D cameras and provide sensor data which describe the surface of the patient 25 as the examination object 10 and possibly of additional objects 16. It should be noted here that the sensor data of the cameras 26 to be evaluated to sensor information in step S1 is to be recorded with the patient 24 already positioned for the recording of the projection images, although the patient must not necessarily yet be within the patient receiving space 25, since information regarding the position of the motor-powered patient table 23 is present in a control device 27 controlling the operation of the computed tomography apparatus 19.

Figure 6:
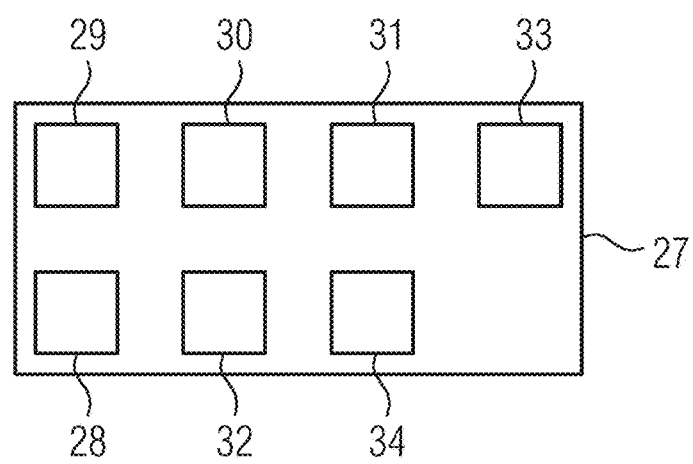
FIG. 6 shows the functional structure of the control device of the computed tomography apparatus of FIG. 5.

The control device 27 is configured for carrying out at least one embodiment of the inventive method, and its functional structure is described in greater detail again by reference to FIG. 6. Accordingly, apart from a recording unit 28, which is in principle known and by which, for example, the recording arrangement and further components are controllable for recording projection images, the control device 27 firstly comprises a sensor information establishing unit 29 by which the sensor information according to step S1 can be established. In a deciding unit 30, the decision according to step S2 can be made. A contour information establishing unit 31 is configured for carrying out the step S4, wherein the contour information establishing unit 31 can already access a general reconstruction unit 32 for the reconstruction of high-dimensional data sets from projection images, in which, for example, different reconstruction algorithms, in particular, also for the reconstruction in the extended field of view 11, can be provided. The contour information establishing unit 31 can access the reconstruction unit 32, for example, for the establishment of a reconstruction data set which is to be taken as a basis for an item of preliminary information.

The forward projection of step S5 can be carried out by a forward projection unit 33, while an enhancing unit 34 is provided for the enhancement of the projection data on the basis of the forward projection, and therefore for carrying out step S6.

The reconstruction unit 32 naturally also serves to carry out the reconstructions in steps S3 and S7.

Although the invention has been illustrated and described in detail with the preferred example embodiment, the invention is not restricted by the examples disclosed and other variations can be derived therefrom by a person skilled in the art without departing from the protective scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstructing an image data set from projection images of an examination object recorded at different projection directions with a computed tomography apparatus, the computed tomography apparatus including a nominal field of view acquired from all projection directions in respective projection images, at least one of the examination object and an additional object associated with the examination object extending partially out of the nominal field of view into an extended field of view, the method comprising:

establishing an item of contour information describing a contour of at least one of the examination object and the additional object;

enhancing projection data of the projection images, based upon the contour information established, by way of forward projection in regions in which at least one of the examination object and the additional object was not acquired in the projection data of a projection image; and reconstructing the image data set based upon the projection data enhanced, wherein, from sensor data of at least one camera, the examination object positioned for recording at least one of the projection images and the additional object is acquired, an item of sensor information at least partially describing at least one of the contour of the examination object and of the additional object being established and used for the establishing of the item of contour information, and wherein, firstly through reconstruction of a provisional reconstruction data set from the original projection images for the extended field of view and threshold value formation, an item of preliminary information provisionally describing at least the contour of at least one of the examination object and of the additional object is established, the item of preliminary information being adapted based upon the item of sensor information.

2. The method of claim 1, wherein the at least one camera configured is a 3D camera.

3. The method of claim 2, wherein the at least one camera configured is a terahertz camera.

4. The method of claim 1, wherein the at least one camera is registered with a recording arrangement of the computed tomography apparatus.

5. The method of claim 1, wherein a portion of the contour of the examination object not acquirable by the at least one camera is established by at least one of extrapolation and interpolation.

6. The method of claim 1, wherein, as contour information, a binary subdivision classifying according to air and at least one of the examination object and additional object at least of the extended field of view is used.

7. The method of claim 1, wherein adapting of the item of preliminary information to the contour information takes place through elastic registration of the item of preliminary information to components of the contour contained in the item of sensor information.

8. The method of claim 1, wherein for each scan, the item of sensor information is automatically checked for portions of at least one of the examination object and the additional object protruding outside the nominal field of view, whereby the reconstruction is automatically triggered with or without an extended field of view.

9. A non-transitory computer readable medium storing program code to carry out the method of claim 1 when the program code is executed on a control device of a computed tomography apparatus.

10. An electronically readable data carrier storing a computer program to carry out the method of claim 1 when program code of the computer program is executed on a control device of a computed tomography apparatus.

11. The method of claim 1, wherein at least one item of 3D information relating to the contour of at least one of the examination object and the additional object is established from at least one of sensor data of at least two differently positioned cameras and sensor data from an item of arrangement information of the camera.

12. The method of claim 11, wherein portions of the contour lying outside an acquisition range of a camera are acquired by at least one further camera.

13. The method of claim 1, wherein from the sensor data, at least one item of object information describing a type of the additional object used, and wherein a three-dimensional computer model is used in the establishing of the item of contour information describing the contour of the additional object.

14. The method of claim 13, wherein, based upon the at least one item of object information, the three-dimensional computer model of the additional object is selected and thereafter the contour of the additional object is adapted, according to at least one of the item of sensor information and item of preliminary information for the establishment of the contour of the additional object in the contour information, to the three-dimensional computer model of the additional object.

15. The method of claim 13, wherein the three-dimensional computer model of the additional object also includes an item of material information describing the attenuation properties for X-ray radiation in the additional object, the material information being taken into account in the forward projection.

16. A method for reconstructing an image data set from projection images of an examination object recorded at different projection directions with a computed tomography apparatus, the computed tomography apparatus including a nominal field of view acquired from all projection directions in respective projection images, at least one of the examination object and an additional object associated with the examination object extending partially out of the nominal field of view into an extended field of view, the method comprising:

establishing an item of contour information describing a contour of at least one of the examination object and the additional object;

enhancing projection data of the projection images, based upon the contour information established, by way of forward projection in regions in which at least one of the examination object and the additional object was not acquired in the projection data of a projection image; and reconstructing the image data set based upon the projection data enhanced, wherein, from sensor data of at least one camera, the examination object positioned for recording at least one of the projection images and the additional object is acquired, an item of sensor information at least partially describing at least one of the contour of the examination object and of the additional object being established and used for the establishing of the item of contour information, and wherein from the sensor data, at least one item of object information describing a type of the additional object used, and wherein a three-dimensional computer model is used in the establishing of the item of contour information describing the contour of the additional object.

17. The method of claim 16, wherein, based upon the at least one item of object information, the three-dimensional computer model of the additional object is selected and thereafter the contour of the additional object is adapted, according to at least one of the item of sensor information and item of preliminary information for the establishment of the contour of the additional object in the contour information, to the three-dimensional computer model of the additional object.

18. The method of claim 17, wherein the three-dimensional computer model of the additional object also includes an item of material information describing attenuation properties for X-ray radiation in the additional object, the item of material information being taken into account in the forward projection.

19. The method of claim 16, wherein the three-dimensional computer model of the additional object also includes an item of material information describing the attenuation properties for X-ray radiation in the additional object, the material information being taken into account in the forward projection.

20. A computed tomography apparatus, comprising:
at least one camera; and
a control device configured for reconstructing an image data set from projection images of an examination object recorded at different projection directions with a computed tomography apparatus, the computed tomography apparatus including a nominal field of view acquired from all projection directions in respective projection images, at least one of the examination object and an additional object associated with the examination object extending partially out of the nominal field of view into an extended field of view, the control device being configured to:
establish an item of contour information describing a contour of at least one of the examination object and the additional object;
enhance projection data of the projection images, based upon the contour information established, by way of forward projection in regions in which at least one of the examination object and the additional object was not acquired in the projection data of a projection image; and
reconstruct the image data set based upon the projection data enhanced,
wherein, from sensor data of at least one camera, the examination object positioned for recording at least one of the projection images and the additional object is acquired, an item of sensor information at least partially describing at least one of the contour of the examination object and of the additional object being established and used for establishing the item of contour information, and
wherein, firstly through reconstruction of a provisional reconstruction data set from the original projection images for the extended field of view and threshold value formation, an item of preliminary information provisionally describing at least the contour of at least one of the examination object and of the additional object is established, the item of preliminary information being adapted based upon the item of sensor information.

* * * * *